United States Patent [19]
Dubief et al.

[11] Patent Number: 6,120,757
[45] Date of Patent: Sep. 19, 2000

[54] AQUEOUS DISPERSION COMPRISING A UV SCREENING AGENT OF ORGANOSILOXANES TYPE CONTAINING A BENZALMALONATE FUNCTION AND A WATER-INSOLUBLE CATIONIC SURFACTANT

[75] Inventors: Claude Dubief, Le Chesnay; Danièle Cauwet-Martin, Paris, both of France

[73] Assignee: Societe L'Oreal S.A., Paris, France

[21] Appl. No.: 09/204,554

[22] Filed: Dec. 3, 1998

[30] Foreign Application Priority Data

Dec. 3, 1997 [FR] France .................................. 97 15243

[51] Int. Cl.[7] .............................. A61K 7/06; A61K 7/42; A61K 7/44; A61K 7/075; A61K 7/00
[52] U.S. Cl. ............................ 424/70.9; 424/59; 424/60; 424/70.1; 424/70.28; 424/401
[58] Field of Search ................................ 424/401, 59, 60, 424/70.1, 70.9, 70.28

[56] References Cited

U.S. PATENT DOCUMENTS

| 4,275,055 | 6/1981 | Nachtigal et al. | 424/70.19 |
|---|---|---|---|
| 5,330,758 | 7/1994 | Hansenne-Richoux et al. | 424/450 |
| 5,415,854 | 5/1995 | Forestier et al. | 424/59 |
| 5,674,511 | 10/1997 | Kacher et al. | 424/401 |
| 5,698,183 | 12/1997 | Langer et al. | 424/59 |
| 5,882,632 | 3/1999 | Allard et al. | 424/59 |

FOREIGN PATENT DOCUMENTS

| 0389337 | 9/1990 | European Pat. Off. |
| 0583888 | 2/1994 | European Pat. Off. |
| 0709080 | 5/1996 | European Pat. Off. |
| 842 965 | 5/1998 | European Pat. Off. |

*Primary Examiner*—Shelley A. Dodson
*Assistant Examiner*—Marina Lamm
*Attorney, Agent, or Firm*—Burns, Doane, Swecker & Mathis, L.L.P.

[57] ABSTRACT

The invention relates to a composition in the form of an aqueous dispersion, characterized in that it comprises, in a cosmetically acceptable medium, at least one liposoluble agent for screening out ultraviolet radiation, of the organosiloxane type containing a benzalmalonate function and at least one water-insoluble cationic surfactant, as well as to its cosmetic uses, in particular for protecting keratin fibres and their natural or artificially dyed color, in particular for protecting human hair against the harmful effects of UV rays.

21 Claims, No Drawings

AQUEOUS DISPERSION COMPRISING A UV SCREENING AGENT OF ORGANOSILOXANES TYPE CONTAINING A BENZALMALONATE FUNCTION AND A WATER-INSOLUBLE CATIONIC SURFACTANT

The invention relates to a composition in the form of an aqueous dispersion, characterized in that it comprises, in a cosmetically acceptable medium, at least one liposoluble agent for screening out ultraviolet radiation, of the organosiloxane type containing a benzalmalonate function and at least one water-insoluble cationic surfactant, as well as to its cosmetic uses, in particular for protecting keratin fibres and their natural or artificially dyed color, in particular for protecting the hair against the harmful effects of UV rays.

It has been known for a long time that light, in particular ultraviolet light, degrades the cosmetic and/or mechanical properties of the hair. The hair then becomes dull, coarse and brittle. Unlike the skin, the hair turns lighter in colour.

Attempts have been made for many years in the cosmetics industry to find substances for protecting the hair against degradation caused by atmospheric attacking factors such as UV radiation, in particular solar radiation. Moreover, it is desired to obtain, at the same time, good cosmetic properties with respect to the hair, such as a soft feel and good disentangling or sheen.

In this respect it has already been proposed to use the sunscreens used for photoprotection of the skin in formulations for hair treatment and haircare. However, the skin and the hair are very different in structure and the Applicant has thus observed that most of the screening agents used in compositions for the skin are not effective for protecting the hair.

Among the sunscreens commonly used in cosmetics there is a distinction between water-soluble screening agents, which generally bear ionic—anionic or cationic—groups, and liposoluble screening agents, which are generally of nonionic nature.

The water-soluble screening agents of anionic type are generally difficult to use in hair formulations containing many types of conditioners such as cationic polymers or cationic surfactants or alternatively thickeners with which they are incompatible.

Hair compositions containing water-soluble screening agents of cationic type in the presence of conditioners of the same polarity have a very limited protective activity on the hair against UV rays on account of competition between the various cationic species for binding to the anionic sites on the keratin fibres.

Moreover, water-soluble screening agents are generally not suitable for so-called rinse-out conditioning compositions; they are easily removed from the hair during the final rinsing step.

The liposoluble screening agents which are generally used in the aqueous hair-treatment compositions of the prior art require solubilization in a fatty phase and/or stabilization using specific emulsifiers.

In particular, rinse-out hair formulations are known containing liposoluble UV screening agents consisting of three phases: an aqueous first phase, a lamellar second phase based on cationic surfactant and on long-chain fatty alcohol, and a fatty third phase containing the liposoluble UV screening agents. These compositions generally lead, after application and rinsing with water, to poor distribution of the liposoluble screening agent on the head of hair and to an insufficient amount of screening agent being deposited to ensure good protection against UV radiation.

To overcome these drawbacks, patent application EP-A-0,419,164 has proposed conditioning hair compositions comprising an aqueous phase and a lamellar phase containing at least one conditioning cationic surfactant and a liposoluble screening agent in the form of an oil, such as 2-ethylhexyl p-methoxycinnamate (sold under the trade name Parsol MCX), 2-ethylhexyl para-dimethylaminobenzoate (sold under the trade name Escalol 507) and/or dihydroxypropyl p-aminobenzoate (sold under the trade name Amerscreen P).

The Applicant has found, surprisingly and unexpectedly, that the use of a water-insoluble cationic surfactant in an aqueous dispersion comprising a liposoluble agent for screening out ultraviolet radiation, of the organosiloxane type containing a benzalmalonate function makes it possible to directly obtain stable, homogeneous aqueous dispersions of the said liposoluble screening agents, which do not have all the technical drawbacks mentioned above.

The Applicant has discovered that the formulations thus obtained can be used in any form of hair formulation and make it possible to obtain amounts of screening agent deposited on the hair which are sufficient to obtain good protection of the head of hair against attack by UV rays and good protection of the colour of natural hair or artificially dyed hair. Furthermore, these formulations provide excellent cosmetic properties, in particular as regards the disentangling, softness or sheen.

The Applicant has discovered that the aqueous dispersions of the invention can be used more particularly in hair compositions whose application to the hair is followed by rinsing with water, and that they give, at the same time, better cosmetic performance, a greater amount of screening agent deposited on the hair, in particular on unsensitized hair, as well as better distribution and better resistance to rinsing than those obtained with the compositions of the prior art containing a standard liposoluble screening agent.

The subject of the present invention is a cosmetic or dermatological composition in the form of an aqueous dispersion comprising, in a cosmetically acceptable medium, at least one water-insoluble cationic surfactant and at least one liposoluble UV screening agent of the organosiloxane type containing a benzalmalonate function.

The subject of the present invention is the use of water-insoluble cationic surfactants in, or for the manufacture of, a hair composition comprising at least one liposoluble UV screening agent of the organosiloxane type containing a benzalmalonate function, which is intended to protect the hair against the effects of UV radiation and to protect the colour of natural or artificially dyed hair.

The subject of the present invention is the use of water-insoluble cationic surfactants in, or for the manufacture of, a hair composition comprising at least one liposoluble UV screening agent of the organosiloxane type containing a benzalmalonate function to improve the deposition and/or binding of the said UV screening agent to the hair.

According to the present invention, the term hair use is understood to mean the application of the composition to the hair in order to wash it and/or treat it and/or condition it.

According to the present invention, the term water-insoluble surfactant is understood to mean surfactants which, at a concentration of 1% A.M. at 25° C., do not give an isotropic transparent solution.

According to the present invention, the liposoluble agents for screening out UV radiation, of the organosiloxane type containing a benzalmalonate function, are preferably-chosen from those comprising at least some units corresponding to one of the two formulae (1) and (2) below:

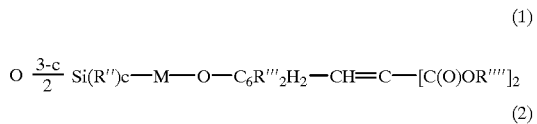

in which:

M denotes a group of structure:

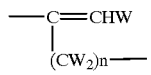

or

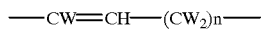

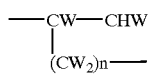

or

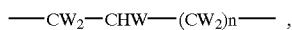

M' denotes a group of structure:
the other silicone units present being of structure:

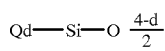

in which R" denotes a $C_1$–$C_8$ alkyl or aryl radical; W is a hydrogen or a $C_1$–$C_5$ alkyl radical; R'" is a hydrogen or a $C_1$–$C_5$ alkyl radical or a radical OW; R"" denotes a $C_1$–$C_5$ alkyl group; Q denotes a hydrogen, a monovalent $C_1$–$C_8$ hydrocarbon-based radical or a halohydrocarbon-based group; c is equal to 0, 1 or 2; d is equal to 0, 1, 2 or 3 and n has a value from 1 to 6; with the proviso that the group —M—O— or —M'—O— is connected to the aromatic ring in a meta or para position relative to the group:

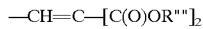

and with the proviso that the two groups R'" occupy the other remaining positions on the aromatic ring.

These screening silicones and processes for their preparation are described in patent applications EP-A-0,392,882, EP-0,538,431, EP-A-0,709,080 and WO 92/20690.

In one particularly preferred embodiment of the invention, one family of compounds which is particularly desired is the one defined by the benzalmalonate silicones chosen from the group consisting of:

(i) silicones corresponding to formula (4) below:

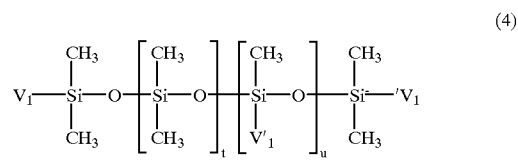

in which:

V'$_1$ denotes the group of structure:

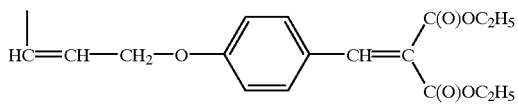

V$_1$ denotes $CH_3$ or V'$_1$;

(ii) silicones corresponding to formula (5) below:

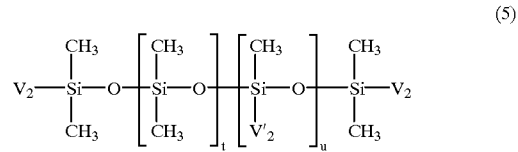

V'$_2$ denotes the group of structure:

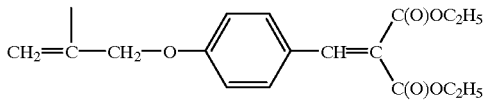

V$_2$ denotes $CH_3$ or V'$_2$;

(iii) mixtures thereof;

with $0 \leq t \leq 100$ and $0 \leq u \leq 20$, with the proviso that:

when V$_1$=V'$_1$ and/or V$_2$=V'$_2$, then u=0; and when V$_1$=$CH_3$ and/or V$_2$=$CH_3$, then $1 \leq u \leq 20$.

The screening organosiloxanes of the invention are preferably used in amounts at least equal to 0.05% by weight, and generally ranging from 0.05 to 10% by weight, and more particularly from 0.1 to 6% by weight, relative to the weight of the composition.

The water-insoluble cationic surfactants are, according to the invention, preferably chosen from the group consisting of quaternary ammonium salts and fatty amines and salts thereof.

Among the fatty amines which can be used according to the invention, mention may be made of dioctylamine, stearyldimethylamine, palmityldimethylamine, oleocetyldimethylamine and amidoamines such as stearylamidoethyldiethylamine, behenylamidopropyldimethylamine, stearylamidopropyldimethylamine, cleylamidopropyldimethylamine and stearylamidoethyldimethylamine.

More particularly, the cationic surfactants of the invention are chosen from:

quaternary ammonium salts corresponding to the general formula (I) below:

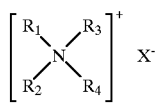
(I)

in which the radicals $R_1$ to $R_4$, which may be identical or different, represent a substituted or unsubstituted aliphatic radical comprising from 1 to about 30 carbon atoms, such as alkyl, alkoxy, polyoxy($C_2$–$C_6$)alkylene, alkylamide, ($C_{12}$–$C_{22}$)alkylamido($C_2$–$C_6$)alkyl, ($C_{12}$–$C_{22}$)-alkylacetate, hydroxyalkyl or an aromatic radical such as aryl or alkylaryl; X is an anion chosen from the group of halides, phosphates, acetates, lactates, alkylsulphates, alkylsulphonates or alkylarylsulphonates;

imidazolinium quaternary ammonium salts such as, for example, that of formula (II) below:

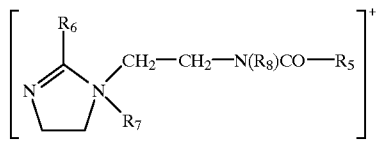
(II)

in which $R_5$ represents an alkenyl or an alkyl radical comprising from 8 to 30 carbon atoms, such as tallow fatty acid derivatives; $R_6$ represents a hydrogen atom, a $C_1$–$C_4$ alkyl radical or an alkenyl or alkyl radical comprising from 8 to 30 carbon atoms; $R_7$ represents a $C_1$–$C_4$ alkyl radical; $R_8$ represents a hydrogen atom or a $C_1$–$C_4$ alkyl radical; X is an anion chosen from the group of halides, phosphates, acetates, lactates, alkylsulphates, alkylsulphonates or alkylarylsulphonates; $R_5$ and $R_6$ preferably represent a mixture of alkenyl and/or alkyl radicals comprising from 12 to 21 carbon atoms, for example tallow fatty acid derivatives, for instance the product sold under the trade name "Rewoquat W 75PG" by the company REWO;

quaternary diammonium salts of formula (III):

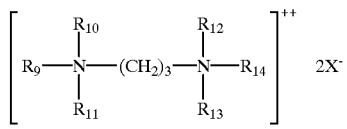
(III)

in which $R_9$ denotes an aliphatic radical comprising about 16 to 30 carbon atoms, $R_{10}$, $R_{11}$, $R_{12}$, $R_{13}$ and $R_{14}$ are chosen from hydrogen or an alkyl radical comprising from 1 to 4 carbon atoms and X is an anion chosen from the group of halides, acetates, phosphates, sulphates, nitrates and methylsulphates. Such quaternary diammonium salts in particular comprise propane tallow diammonium dichloride.

Among the quaternary ammonium salts of formula (I), the ones which will be used more particularly are, on the one hand, the tetraalkylammonium chlorides such as, for example, dialkyldimethylammonium or alkyltrimethylammonium chlorides, in which the alkyl radical comprises from about 12 to about 30 carbon atoms, in particular distearyldimethylammonium chloride or benzyldimethylstearylammonium chloride.

The water-insoluble cationic surfactants are preferably used in amounts generally ranging from 0.05 to 10% by weight, and more particularly from 0.1 to 6% by weight, relative to the weight of the composition.

According to one particularly preferred embodiment of the invention, the compositions of the invention have a pH of greater than or equal to 3, more preferably a pH ranging from 4 to 8 and even more preferably from 4 to 6.

The compositions of the invention generally comprise at least one aqueous phase and one fatty phase consisting either solely of the screening organosiloxane (s) of the invention, or of a mixture thereof with one or more fatty substances chosen from mineral, plant animal or synthetic oils; silicone oils with a linear or cyclic structure, such as polyalkylsiloxanes polyarylsiloxanes, polyalkylarysiloxanes or polyorganosiloxanes modified with non-chromophoric organofunctional groups; silicone gums, resins or waxes, as well as mixtures thereof.

The compositions with which the invention is concerned can be prepared according to the techniques well known to those skilled in the art, in particular those intended for the preparation of dispersions with an aqueous continuous phase such as emulsions of oil-in-water type, gels and cream-gels. They can also be in the form of a simple or complex emulsion (O/W, W/O, O/W/O or W/D/W).

The compositions according to the invention can be in the form of creams, milks, gels, cream-gels, nonionic vesicle dispersions or lotions. The composition in accordance with the invention can also be in the form of a spray or can be pressurized in aerosol devices.

In addition to water, the aqueous phase can contain one or more standard cosmetic organic solvents such as a lower alcohol containing 1 to 4 carbon atoms, and preferably ethanol or isopropanol, or other alcohols such as alkylene glycols or glycol ethers.

The compositions in accordance with the invention can also contain any other additive usually applied to keratin fibres, and in particular human hair, such as, for example, dyes, surfactants, polymers, thickeners, conditioners, opacifiers, pearlescent agents, antidandruff agents, agents for preventing hair loss, ceramides. vitamins, anti-oxidants, fragrances, preserving agents and softeners, as well as other screening agents.

Needless to say, a person skilled in the art will take care to select the optional complementary compound(s) mentioned above and/or the amounts thereof such that the advantageous properties intrinsically associated with the combination [screening organosiloxane+cationic surfactant] in accordance with the invention are not, or are not substantially, adversely affected by the addition (s) envisaged.

The compositions of the invention which are intended to be applied to keratin fibres, and in particular human hair, are rinse-out products such as shampoos or conditioners, to be applied before or after dyeing or bleaching or before or after permanent-waving or straightening of the hair, or alternatively leave-in products such as a styling or treating lotion or gel or a blow-drying or hairsetting lotion or gel; permanent-waving or hair-straightening products; products for dyeing or bleaching the hair.

The subject of the present invention is also a cosmetic treatment process for protecting the hair against the effects of UV rays and for protecting the natural or artificially dyed colour of the hair, this process consisting in applying to the hair an effective amount of a composition in the form of an aqueous dispersion comprising at least one liposoluble UV screening agent of the organosiloxane type containing a benzalmalonate function and at least one water-insoluble cationic surfactant as defined above.

The examples which follow serve to illustrate the invention without, however, being limiting in nature.

EXAMPLE 1

Antisun Formulation

| | |
|---|---|
| Organosiloxane containing a benzalmalonate function of formula (4) or (5) | 1 g |
| Behenyldimethylbenzylammonium chloride sold under the name Ammonyx 4022 (Goldschmidt) | 5 g AM |
| Preserving agent, fragrance qs | |
| Water    qs | 100 g |

EXAMPLE 2

Antisun Formulation

| | |
|---|---|
| Organosiloxane containing a benzalmalonate function of formula (4) or (5) | 0.5 g |
| 1-Methyl-2-tallow-3-tallowamidoethyl-imidazolium methosulphate at 75% in propylene glycol, sold under the name Rewoquat W75PG (REWO) | 2 g AM |
| Preserving agent, fragrance qs | |
| Water    qs | 100 g |

COMPARATIVE EXAMPLE 2

| | |
|---|---|
| 2-Ethylhexyl p-methoxycinnamate in the form of an oil (sold under the trade name Parsol MCX) | 0.5 g |
| 1-Methyl-2-tallow-3-tallowamidoethyl-imidazolium methosulphate at 75% in propylene glycol sold under the name Rewoquat W75PG (REWO) | 2 g AM |
| Preserving agent, fragrance qs | |
| Water    qs | 100 g |

COMPARATIVE TESTS

1. Deposition of Screening Agent on Hair

The deposition of silicone screening agent of the invention on natural hair after applying the composition of Example 2 and rinsing with water was measured. This deposition was compared with that of 2-ethylhexyl p-methoxycinnamate in oil form obtained with the composition of Comparative Example 2.

PROCEDURE

The amount of UV screening agent deposited on the hair is measured by measuring the absorbance of the UV screening agent at the characteristic wavelength, by spectrophotometer. The concentration of the screening agent is calculated from a pre-established calibration curve.

The locks of hair used consist of a weight of about 1 g of natural chestnut-brown hair containing 90% white hairs. The spectrophotometer used is of the Shimatzu UV 2100 (Roucaire) type. The screening agent studied, fixed to the hair, is extracted into dichloromethane. The tests are carried out on 4 samples for each test formulation and 2 samples for the control placebo formulation.

Each 1 g lock is introduced into a 30 ml pillbox. 25 ml of dichloromethane are added. The pillboxes are placed under mechanical agitation for 2 hours; 170 movements/minute (Heidolf Promax 2020 agitator). The lock is lifted above the level of liquid with tweezers; it is left to drain for 15 seconds.

A calibration curve is established with amounts of from 1 to 10 mg of screening agent. The response should be linear of the type Y=aX+b with X representing the concentration of the screening agent in the solution extracted, as mg/g of hair. The amounts of screening agents are weighed out in 100 ml graduated flasks which are filled to the mark with the solvent. After dissolution, the absorbance of the screening agent in each solution at its characteristic wavelength, as well as that of a solvent-based control solution, are measured in 115B-QS cuvettes (10 mm optical path length) for spectrophotometry. An assay of the screening agent deposited on the lock with the extraction solution for the lock treated with the antisun formulation containing the screening agent is then carried out for each sample. The average absorbance of the screening agent in 25 ml of dichloromethane (optical density) is calculated. The concentration of the screening agent deposited on the hair is deduced from the calibration curve.

The results are summarized in the following table:

| COMPOSITION | Calibration curve obtained | Average optical density | Amount of screening agent deposited (mg/g of hair) |
|---|---|---|---|
| Example 2 | Y = 0.02 + 0.77 X | 1.68 | 2.14 |
| Comparative Example 2 | Y = 0.6 + 3.84 X | 2.35 | 0.6 |

More than 3 times as much of the screening agent compound according to the invention as of the standard 2-ethylhexyl p-methoxycinnamate liposoluble screening agent is deposited.

2. Cosmetic Properties

In a sensory evaluation test, 10 control individuals judged that the composition of Example 2 according to the invention, after application to the hair, led to a markedly less greasy, less laden and more pleasant feel than the composition of Comparative Example 2.

What is claimed is:

1. A cosmetic or dermatological composition that is in the form of an aqueous dispersion which comprises:

(i) an effective amount of at least one liposoluble organosiloxane UV screening agent compound that comprises at least one benzalmalonate functional group; and (ii) at least one water-insoluble cationic surfactant that is sufficient to improve the deposition and/or adherence of said liposoluble UV screening agent upon topical application of said composition to the hair.

2. A composition according to claim 1, wherein said liposoluble organosiloxane UV screening agent containing a benzalmalonate function, comprises at least one unit having formulae (1) and (2) below:

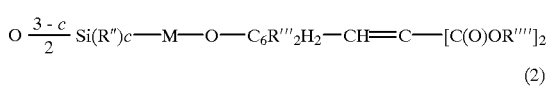 (1)

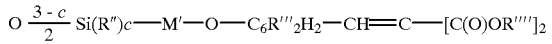 (2)

in which

M has the following structure:

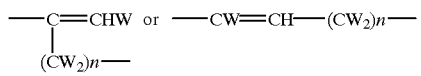

M' has the following structure:

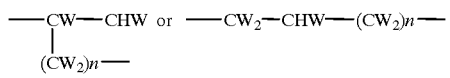

the other silicone units have the following structure:

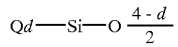 (3)

in which R' is a $C_1$–$C_8$ alkyl or aryl radical; W is a hydrogen or a $C_1$–$C_5$ alkyl radical; R''', is a hydrogen or a $C_1$–$C_5$ alkyl radical or a radical OW; R'''' is a $C_1$–$C_5$ alkyl group; Q is a hydrogen, a monovalent $C_1$–$C_8$ hydrocarbon-based radical or a halohydrocarbon-based group; c is equal to 0, 1 or 2; d is equal to 0, 1, 2 or 3 and n has a value from 1 to 6; with the proviso that the group-M—O— or —M'—O— is connected to the aromatic ring in a meta or para position relative to the group:

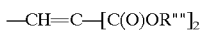

and with the further proviso that the two groups R''' occupy the remaining positions on the aromatic ring.

3. A composition according to claim 1, wherein said liposoluble organosiloxane UV screening agent containing a benzalmalonate function, is selected from the group consisting of:

(i) silicones having formula (4) below:

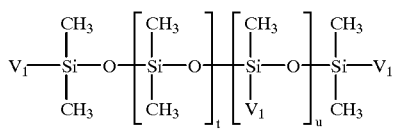 (4)

in which $V'_1$ has the following structure:

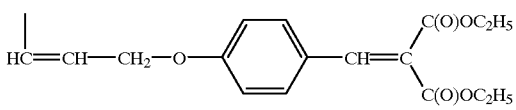

$V_1$ is $CH_3$ or $V'_1$;

(ii) silicones having formula (5) below:

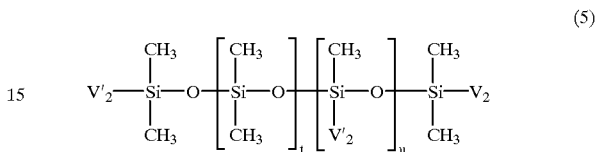 (5)

$V'_2$ has the following structure:

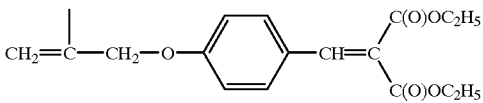

$V_2$ is $CH_3$ or $V'_2$;

(iii) mixtures thereof;

with $0 \leq t \leq 100$ and $0 \leq u \leq 20$, with the proviso that:

when $V_1=V'_1$ and/or $V_2=V'_2$, the u=0; and when $V_1$ –$CH_3$ and/or $V_2=CH_3$, then $1 \leq u \leq 20$.

4. A composition according to claim 1, wherein said liposoluble organosiloxane UV screening agent containing a benzalmalonate function, is present in an amount ranging from 0.05 to 10% by weight relative to the weight of the composition.

5. A composition according to claim 1, in which said water-insoluble cationic surfactant is selected from the group consisting of quaternary ammonium salts, fatty amines and salts thereof.

6. A composition according to claim 5, wherein said fatty amines are selected from the group consisting of dioctylamine, stearyldimethylamine, pelmityldimethylamine, oleocetyldimethylamine and amidoamines.

7. A composition according to claim 5, wherein said water-insoluble cationic surfactant is selected from the group consisting of:

quaternary ammonium salts having the general formula (I) below:

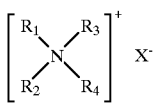 (I)

in which the radicals $R_1$ to $R_4$, which may be identical or different, represent a substituted or unsubstituted aliphatic radical comprising from 1 to about 30 carbon atoms, or an aromatic radical; X is an anion selected from the group consisting of halides, phosphates, acetates, lactates, alkylsulphates, alkylsulphonates and alkylarylsulphonates;

imidazolinium quaternary ammonium salts

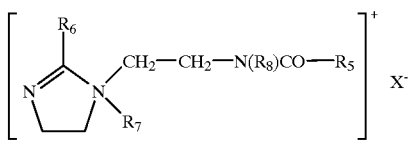

in which $R_5$ is an alkenyl or an alkyl radical comprising from 8 to 30 carbon atoms; $R_6$ is a hydrogen atom, a $C_1$–$C_4$ alkyl radical or an alkenyl or alkyl radical comprising from 8 to 30 carbon atoms; $R_7$ is a $C_1$–$C_4$ alkyl radical; $R_8$ is a hydrogen atom or a $C_1$–$C_4$ alkyl radical; X is an anion selected from the group consisting of halides, phosphates, acetates, lactates, alkylsulphates, alkylsulphonates or alkylarylsulphonates;

quaternary diammonium salts of formula (III):

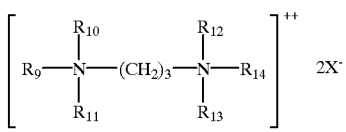

in which $R_9$ is an aliphatic radical comprising about 16 to 30 carbon atoms, $R_{10}$, $R_{11}$, $R_{12}$, $R_{13}$ and $R_{14}$ are selected from the group consisting of hydrogen and an alkyl radical comprising from 1 to 4 carbon atoms and X is an anion selected from the group consisting of halides, acetates, phosphates, sulphates, nitrates and methylsulphates.

8. A composition according to claim 1, wherein said water-insoluble cationic surfactant is used in an amount ranging from 0.05 to 10% by weight relative to the weight of the composition.

9. A composition according to claim 1 having a pH ranging from 3 to 8.

10. A composition according to claim 1, which comprises at least one aqueous phase and one fatty phase consisting either solely of said liposoluble organosiloxane, UV screening agent or a mixture containing said screening agent and further comprising one or more fatty substances selected from the group consisting of mineral, plant, animal or synthetic oils; silicone oils comprising a linear or cyclic structure, silicone gums, resins or waxes, and mixtures thereof.

11. A composition according to claim 1 which is in the form of a cream, a milk, a cream-gel, a nonionic vesicle dispersion, a lotion, a spray or a pressurized form contained in an aerosol device.

12. A composition according to claim 1 which further contains one or more cosmetic additives selected from the group consisting of dyes, surfactants, polymers, thickeners, conditioners, opacifiers, pearlescent agents, antidandruff agents, agents for preventing hair loss, ceramides, vitamins, antioxidants, fragrances, preserving agents, softeners, and other screening agents.

13. A composition according to claim 1 which is suitable for usage as a hair care product.

14. The composition of claim 4, which comprises 0.1 to 6% by weight of said screening agent.

15. The composition of claim 7, wherein said imidazolinium quaternary ammonium salt has formula II below:

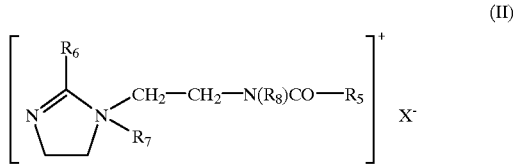

in which $R_5$ is an alkenyl or an alkyl radical comprising from 8 to 30 carbon atoms; $R_6$ is a hydrogen atom selected from the group consisting of, a $C_1$–$C_4$ alkyl radical and an alkenyl or alkyl radical comprising from 8 to 30 carbon atoms; $R_7$ is a $C_1$–$C_4$ alkyl radical; $R_8$ is a hydrogen atom or a $C_1$–$C_4$ alkyl radical; X is an anion selected from the group consisting of halides, phosphates, acetates, lactates, alkylsulphates, alkylsulphonates and alkylarylsulphonates.

16. The composition of claim 8, wherein the amount of said water-insoluble cationic surfactant ranges from 0.1 to 6% by weight.

17. The composition of claim 9, which has a pH ranging from 4 to 6.

18. The composition of claim 7, wherein said aliphatic radical having about 1 to 30 carbon atoms is selected from the group consisting of alkyl, alkoxy, polyoxy ($C_2$–$C_6$) alkylene, alkylamide, ($C_{12}$–$C_{22}$)alkylamido($C_2$–$C_6$)alkyl, ($C_{12}$–$C_{22}$)-alkylacetate, and hydroxy alkyl and said aromatic radical is an aryl or alkylaryl group.

19. The composition according to claim 6, wherein said amidoamines is selected from the group consisting of stearylamidoethyldiethylamine, behenylamidopropyldimethylamine, steaiylamidopropyldimethylamine, oleylamidopropyldmethylamine and stearylamidoethyldmethylamine.

20. A method for protecting the hair against the effects of UV rays and for protecting its natural or artificially dyed color, said method comprising topically applying to the hair an effective amount of a composition according to claim 1.

21. A method for improving the deposition and adhesion to the hair of a cosmetic or dermatological composition containing at least one liposoluble organosiloxane UV screening agent comprising at least one benzalmalonate function that is in the form of an aqueous dispersion by adding to said composition an amount of at least one water-insoluble cationic surfactant effective to enhance the deposition and adhesion of said screening agent upon application of said composition to the hair.

* * * * *